United States Patent
Abe et al.

(10) Patent No.: US 8,420,845 B2
(45) Date of Patent: Apr. 16, 2013

(54) FUNCTIONAL SUBSTANCE-RELEASING AGENT

(75) Inventors: Hideyuki Abe, Wakayama (JP); Makiko Shigehisa, Berlin (DE)

(73) Assignee: Kao Corporation, Tokyo (JP)

( * ) Notice: Subject to any disclaimer, the term of this patent is extended or adjusted under 35 U.S.C. 154(b) by 218 days.

(21) Appl. No.: 12/918,267

(22) PCT Filed: Feb. 18, 2009

(86) PCT No.: PCT/JP2009/053301
§ 371 (c)(1),
(2), (4) Date: Oct. 5, 2010

(87) PCT Pub. No.: WO2009/104797
PCT Pub. Date: Aug. 27, 2009

(65) Prior Publication Data
US 2011/0028366 A1  Feb. 3, 2011

(30) Foreign Application Priority Data
Feb. 19, 2008 (JP) .................... 2008-37430

(51) Int. Cl.
*C07F 7/04* (2006.01)

(52) U.S. Cl.
USPC ........................................... 556/482; 512/25

(58) Field of Classification Search ............... 512/25; 556/482
See application file for complete search history.

(56) References Cited

U.S. PATENT DOCUMENTS

| | | | |
|---|---|---|---|
| 2,995,590 A | 8/1961 | Peeler et al. | |
| 3,271,305 A | 9/1966 | Allen et al. | |
| 4,500,725 A | 2/1985 | Yemoto et al. | |
| 4,880,851 A | 11/1989 | Yamamoto | |
| 5,856,543 A | 1/1999 | Friedrich et al. | |
| 6,083,901 A | 7/2000 | Perry et al. | |
| 6,225,391 B1 | 5/2001 | Parthasarathy et al. | |
| 2004/0072704 A1 | 4/2004 | Gerke et al. | |
| 2005/0136021 A1 | 6/2005 | Perry et al. | |
| 2009/0099382 A1 | 4/2009 | Gerke et al. | |

FOREIGN PATENT DOCUMENTS

| | | | |
|---|---|---|---|
| EP | 0 737 688 A2 | 10/1996 | |
| EP | 1 857 096 A2 | 11/2007 | |
| GB | 2007703 A | 5/1979 | |
| GB | 2319527 A | 5/1998 | |
| JP | 54-59498 A | 5/1979 | |
| JP | 54-93006 A | 7/1979 | |
| JP | 58-22063 A | 2/1983 | |
| JP | 63-260567 A | 10/1988 | |
| JP | 7-268383 A | 10/1995 | |
| JP | 10-237175 A | 9/1998 | |
| JP | 2000-297292 A | 10/2000 | |
| JP | 2001-512772 A | 8/2001 | |
| JP | 2003-526644 A | 9/2003 | |
| JP | 2007-518713 A | 7/2007 | |
| WO | WO 2007/101612 A1 | 9/2007 | |

OTHER PUBLICATIONS

Japanese Office Action dated Oct. 4, 2011 for Application No. 2008-037430.
Extended European Search Report dated Feb. 16, 2011 for Application No. 09712942.3.
International Search Report for PCT/JP2009/053301; mailed on Jun. 2, 2009.
International Preliminary Report on Patentability and Written Opinion of the International Searching Authority mailed Oct. 5, 2010 for International Application No. PCT/JP2009/053301.
Chinese Office Action mailed Oct. 8, 2012 in connection with corresponding Chinese Application No. 200980105711.2.

*Primary Examiner* — John Hardee
(74) *Attorney, Agent, or Firm* — Birch Stewart Kolasch & Birch, LLP

(57) ABSTRACT

Disclosed are: a functional material release agent including 35% to 95% by mass of the silicate ester compound represented by formula (1) and 0% to 40% by mass of the silicate ester compound represented by formula (2); a method for manufacturing the release agent; and compositions containing the release agent. (In the formula, $R^1$ is an aliphatic hydrocarbon group with a total of 4 to 22 carbon atoms, that may contain a phenyl group, a hydroxyl group, or an alkoxy group as a substituent; $R^2$ is the residue of functional alcohol minus one hydroxyl group; and $R^3$ is a hydrogen atom or an alkyl group with one to six carbon atoms.)

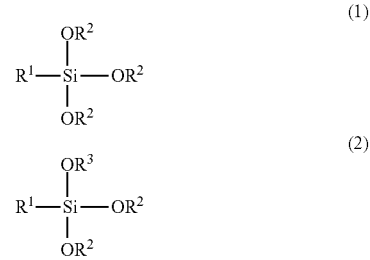

13 Claims, No Drawings

FUNCTIONAL SUBSTANCE-RELEASING AGENT

FIELD OF THE INVENTION

The present invention relates to a functional substance-releasing agent containing a silicate ester compound that releases a functional substance, such as a fragrant material, an antibacterial agent and an antifungal agent, being useful to add to various products, a method for producing the same, and a composition containing the functional substance-releasing agent.

BACKGROUND OF THE INVENTION

In a blended fragrance, aromatic components having different volatilization properties, which are so-called top-note, middle-note and base-note, are blended to give a desired aroma. Such a blended fragrance has a problem of being unable to give and keep an aroma unchanged for a long time, because more volatile component preferentially volatilizes to change an aroma of the blended fragrance over time. To solve the problem, there is a known gelled aromatic composition prepared by microencapsulating a fragrant material and dispersing it in a gel base material (JP-A 63-260567). However, the method is effective for producing a gel preparation, but is difficult to be applied in production of liquid preparation of low viscosity, because microcapsules float on the surface or sink to the bottom of a product and are difficult to be formulated stably in the product.

There are also known compositions including a knitted or woven fabric treatment composition, a detergent composition, and a fragrance, that contain silicate esters derived from fragrance alcohol materials and organosilicon compounds such as methyltriethoxysilane (JP-A 54-59498, JP-A 54-93006, and JP-A 58-22063). However, these compositions have low hydrophobicity, and when used in water-containing products such as a detergent and a fragrance, the silicate esters are decomposed and cannot remain effective.

There is also a known silicate ester mixture that can be used in water-containing products such as a detergent, containing polyalkoxysiloxane having higher hydrolysis resistance (JP-A 2003-526644). However, this silicate ester mixture contains a polymer compound, and thus has a problem in compatibility such as solubility in use in various products such as a detergent and a fragrance.

The same problem of decomposition of a fragrant material in products is equally true of volatile antibacterial and antifungal agents. It has been difficult to balance durability of effects with compatibilities of agents.

SUMMARY OF THE INVENTION

The present invention provides a functional substance-releasing agent containing a silicate ester compound represented by the formula (1) (hereinafter referred to as silicate ester compound (1)) in an amount of 35 to 95% by mass and a silicate ester compound represented by the formula (2) (hereinafter referred to as silicate ester compound (2)) in an amount of 0 to 40% by mass, a method for producing the functional substance-releasing agent, and a composition containing the functional substance-releasing agent.

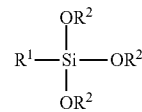

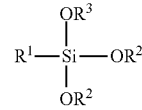

(wherein, $R^1$ represents an aliphatic hydrocarbon group having 4 to 22 carbon atoms in total that may be substituted with phenyl, hydroxyl or an alkoxy group; $R^2$ represents a residual group excluding a hydroxy group from a functional alcohol, and a plurality of $R^2$s may be the same as or different from one another; and $R^3$ represents a hydrogen atom or an alkyl group having 1 to 6 carbon atoms.)

The present invention also provides use of a composition containing the silicate ester compounds (1) and (2) as a functional substance-releasing agent.

DETAILED DESCRIPTION OF THE INVENTION

The present invention provides a functional substance-releasing agent that can be stably formulated in any preparation of any form for any application and can gradually release the functional substance at a constant level for a long time in practical use, a method for producing the same, and a composition containing the functional substance-releasing agent.

The functional substance-releasing agent of the present invention is a new functional substance-releasing agent containing the silicate ester compounds (1) and (2) at a specific ratio, can be stably formulated in any preparation of any form for any application, and can gradually release the functional substance at a constant level for a long time in practical use. The composition containing the functional substance-releasing agent of the present invention can sustain release of the functional substance such as a fragrance alcohol and an antibacterial alcohol for a long time to sustain a constant effect such as an aroma and an antibacterial effect for a long time.

In the silicate ester compounds (1) and (2), $R^1$ represents an aliphatic hydrocarbon group having 4 to 22 carbon atoms in total that may be substituted with phenyl, hydroxyl or an alkoxy group. $R^1$ preferably represents a linear or branched alkyl or alkenyl group having 4 to 22 carbon atoms in total, more preferably a linear or branched alkyl group having 6 to 18 carbon atoms, even more preferably a liner alkyl group having 6 to 18 carbon atoms, such as an n-hexyl, an n-octyl, an n-decyl, an n-dodecyl, an n-hexadecyl, and an n-octadecyl groups, even more preferably a liner alkyl group having 8 to 18 carbon atoms, and even more preferably a liner alkyl group having 10 to 18 carbon atoms, which may be substituted with phenyl, hydroxyl or an alkoxy group.

In the silicate ester compounds (1) and (2), $R^2$ represents a residual group excluding a hydroxy group from a functional alcohol. In the silicate ester compounds (1) and (2), a plurality of $R^2$s may be same or different.

Examples of the functional alcohol constructing $R^2$ include fragrance alcohols as a component used in a blended fragrance, antibacterial alcohols having antibacterial and antifungal properties, moisture retaining alcohols, physiological active alcohols, coloring alcohols and surface-modifying alcohols having usual surface activating properties. Preferred are fragrance alcohols and antibacterial alcohols, and more preferably are fragrance alcohols.

The functional alcohol preferably has 3 to 40, and more preferably 3 to 15 carbon atoms. Specific examples of the functional alcohol include n-hexanol, trans-2-hexenol, fresh leaf alcohol (cis-3-hexenol), 3-octanol, 1-octen-3-ol, 2,6-dimethyl-2-heptanol, 2,4-dimethyl-3-cyclohexene-1-methanol, 4-isopropylcyclohexanol, 4-isopropylcyclohexylmethanol, 1-(4-isopropylcyclohexyl)ethanol, p-tert-butylcyclohexanol, o-tert-butylcyclohexanol, 4-methyl-3-decen-5-ol, 9-decenol, 10-undecenol, linalool, geraniol, nerol, citronellol, rhodinol, dimethyloctanol, hydroxycitronellol, tetrahydrogeraniol, tetrahydrolinalool, lavandulol, mugol, myrcenol, terpineol, L-menthol, borneol, isopulegol, tetrahydromugol, nopol, farnesol, nerolidol, ambrinol, 1-(2-tert-butylcyclohexyloxy)-2-butanol, pentamethylcyclohexylpropanol, 1-(2,2,6-trimethylcyclohexyl)-3-hexanol, santalol, 3,7-dimethyl-7-methoxyoctan-2-ol, 3-methyl-5-(2,2,3-trimethyl-3-cyclopenten-1-yl)-2-pentanol, 2-ethyl-4-(2,2,3-trimethyl-3-cyclopenten-1-yl)-2-butenol, 2-methyl-4-(2,2,3-trimethyl-3-cyclopenten-1-yl)-2-butenol, 2-methyl-4-(2,2,3-trimethyl-3-cyclopenten-1-yl)-1-butanol, 3-methyl-5-(2,2,3-trimethyl-3-cyclopenten-1-yl)-4-penten-2-ol, 3,3-dimethyl-5-(2,2,3-trimethyl-3-cyclopenten-1-yl)-4-penten-2-ol, cedrol, vetiverol, patchouli alcohol, benzyl alcohol, β-phenylethyl alcohol, γ-phenylpropyl alcohol, cinnamic alcohol, anise alcohol, dimethylbenzylcarbinol, methylphenylcarbinol, dimethylphenylcarbinol, phenoxyethyl alcohol, styrallyl alcohol, dimethylphenylethylcarbinol, thymol, carvacrol, eugenol, isoeugenol, ethylvanillin, m-chloroxylenol, 2,4-dichlorophenol, 2,4-dichlorobenzyl alcohol, hinokithiol, 3-methyl-4-isopropylphenol, 2,2-dimethyl-3-(3-methylphenyl)propanol, 3-methyl-5-phenylpentanol, phenylethylmethylethylcarbinol, triclosan, capsaicin, tocopherol, glycerol monolaurate, tri(hydroxymethyl)nitromethane, 2-bromo-2-nitropropan-1,3-diol, 1,3-bis(hydroxymethyl)-5,5'-dimethylhydantoin, and hexahydro-1,3,5-tris(hydroxyethyl)-S-triazine.

Among these functional alcohols, preferred are fragrance alcohols having 5 to 15 carbon atoms and antibacterial alcohols having 3 to 15 carbon atoms, and more preferred are fragrance alcohols having 5 to 15 carbon atoms.

The fragrance alcohol having 5 to 15 carbon atoms are described in, for example, "Gousei Kouryou (synthetic fragrant material), Kagaku Kougyou Nippousya (Chemical Daily)." Specific examples thereof include saturated and unsaturated liner and branched alcohols such as a fresh leaf alcohol (cis-3-hexenol), 3-octenol (1-octen-3-ol), 9-decenol, geraniol, nerol, citronellol, rhodinol, farnesol, hydroxycitronellol, 3,7-dimethyl-7-methoxyoctan-2-ol, 3-methyl-5-(2,2,3-trimethyl-3-cyclopenten-1-yl)-2-pentanol, 2-ethyl-4-(2,2,3-trimethyl-3-cyclopenten-1-yl)-2-butenol, 2-methyl-4-(2,2,3-trimethyl-3-cyclopenten-1-yl)-2-butenol, 2-methyl-4-(2,2,3-trimethyl-3-cyclopenten-1-yl)-1-butanol, 3-methyl-5-(2,2,3-trimethyl-3-cyclopenten-1-yl)-4-penten-2-ol, and 3,3-dimethyl-5-(2,2,3-trimethyl-3-cyclopenten-1-yl)-4-penten-2-ol; aromatic alcohols such as benzyl alcohol, 2-phenylethanol (β-phenylethyl alcohol), cinnamic alcohol, γ-phenylpropyl alcohol, anise alcohol, phenoxyethyl alcohol, styrallyl alcohol, 3-methyl-5-phenylpentanol, and 2,2-dimethyl-3-(3-methylphenyl)-propanol; and saturated and unsaturated cyclic alcohols such as 2,4-dimethyl-3-cyclohexene-1-methanol, 4-isopropylcyclohexylmethanol, 1-(4-isopropylcyclohexyl)ethanol, p-tert-butylcyclohexanol, o-tert-butylcyclohexanol, L-menthol, 1-(2-tert-butylcyclohexyloxy)-2-butanol, pentamethylcyclohexylpropanol, 1-(2,2,6-trimethylcyclohexyl)-3-hexanol, santalol, and vetiverol.

Examples of the antibacterial alcohols having 3 to 15 carbon atoms include alcohols used for antibacterial and antifungal purposes described in "Nihon Boukin Boubai-zai Jiten (handbook of Japan antibacterial and antifungal agents), Nihon Boukin Boubai Gakkai (Society for Antibacterial and Antifungal Agents, Japan)." Specific examples thereof include glycerol monolaurate, tri(hydroxymethyl)nitromethane, 2-bromo-2-nitropropan-1,3-diol, 1,3-bis(hydroxymethyl)-5,5'-dimethylhydantoin, and hexahydro-1,3,5-tris(hydroxyethyl)-S-triazine.

In the functional substance-releasing agent of the present invention, a content of the silicate ester compound (1) is 35 to 95% by mass. The functional substance-releasing agent containing larger amount of the silicate ester compound (1) has higher hydrophobicity and can more effectively prevent decomposition of the silicate ester compound (1) in water-containing products such as a detergent and a fragrance, resulting in more lasting effects. A content of the silicate ester compound (1) is preferably 40 to 95% by mass, more preferably 45 to 95% by mass, and even more preferably 50 to 90% by weight.

In the functional substance-releasing agent of the present invention, a content of the silicate ester compound (2) is 0 to 40% by mass. From the points of reduction of an amount of the functional substance contained therein and reduction of hydrophobicity, the content is preferably 0.5 to 35% by mass, and more preferably 10 to 30% by mass. The contents of the silicate ester compounds (1) and (2) are determined without consideration of a functional alcohol, a compound represented by the formula (3) and a trihalogenated silane represented by the formula (4), which are used as raw materials for production. In other words, the contents represent amounts in silicate ester compounds esterified with the functional alcohol.

The functional substance-releasing agent of the present invention can be produced by the method 1 or 2 described below.

Method 1:

Interesterification between a compound represented by the following formula (3) (hereinafter, referred to as compound (3)):

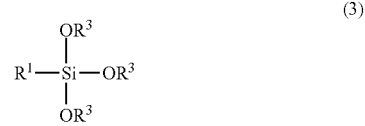

(3)

(wherein, $R^1$ and $R^3$ represent the same meaning as above; and three $R^3$s may be same or different) and a functional alcohol.

Method 2:

Esterification of a trihalogenated silane represented by the following formula (4) (hereinafter, referred to as trihalogenated silane (4)):

(4)

(wherein, $R^1$ represents the same meaning as above; and X represents a halogen atom) with a functional alcohol.

In the method 1, $R^3$ of the formula (3) represents a hydrogen atom or an alkyl group having 1 to 6 carbon atoms. From the point of ease of availability, $R^3$ preferably represents a methyl or ethyl group, and more preferably an ethyl group.

In the interesterification between the compound (3) and a functional alcohol, reaction products have different substitution degrees, depending on a molar ratio of the functional alcohol added to the compound (3). A molar ratio of the functional alcohol to the compound (3) is preferably 0.1 to 10, more preferably 1 to 5, even more preferably 2 to 4, and even more preferably 2.5 to 3.

In the method 1, a reaction temperature of interesterification is preferably not higher than boiling points of the compound (3) and the functional alcohol, more preferably a room temperature (20° C.) to 200° C., even more preferably 50 to 170° C., even more preferably 70 to 150° C., and even more preferably 90 to 130° C.

In the method 1, interesterification is preferably conducted under reduced pressure, from the points of fast progress of the reaction and the like. A degree of pressure reduction, which may be varied according to a reaction temperature, is only required such that the reaction occurs at a temperature not higher than boiling points of the compound (3) and the functional alcohol, and preferably 1.3 Pa to a normal pressure (0.1 MPa), more preferably 130 Pa to 40 kPa, and even more preferably 1.3 kPa to 13 kPa. A pressure applied on the reaction may be reduced at the start or in the middle of the reaction.

In the method 1, a reaction system of interesterification preferably contains a catalyst, from the points of fast progress of the reaction and the like. Examples of the catalyst include alkali catalysts such as sodium hydroxide, potassium hydroxide, sodium methoxide, sodium ethoxide, potassium methoxide, and potassium ethoxide; and Lewis acid catalysts such as aluminium tetraisopropoxide and titanium tetraisopropoxide.

In the method 2, X of the formula (4) represents a halogen atom. Examples of the halogen atom include a chlorine, a bromine, and an iodine atoms. Preferred is a chlorine atom.

In the esterification of the trihalogenated silane (4) with a functional alcohol, reaction products have different substitution degrees, depending on a molar ratio of the functional alcohol added to the trihalogenated silane (4). A molar ratio of the functional alcohol to trihalogenated silane (4) is preferably 0.1 to 10, more preferably 1 to 5, even more preferably 2 to 4, and even more preferably 2.7 to 3.3.

In the method 2, since an acid is generated as a by-product with progresses of the reaction, the reaction is preferably conducted with addition of a base. Examples of the base used include tertiary amines such as triethylamine and pyridine.

From the points of generation of a large amount of salts as by-products, esterification of the method 2 may be performed using a solvent. A reaction temperature can be set at such a low temperature as the substrate and the solvent are not solidified. After the reaction ended, if the solvent must be removed, it can be removed with various known apparatus and devices. Desalting can be performed by known methods such as filtration, extraction, and electrodialysis.

The functional substance-releasing agent of the present invention, produced by interesterification of the method 1 or esterification of the method 2, may contain a silicate ester compound having a different substitution degree from the silicate ester compounds (1) and (2) and a linear or cyclic polymer/condensate of siloxane in addition to the silicate ester compounds (1) and (2). The interesterification of the method 1 and the esterification of the method 2 can be performed with a mixture of two or more functional alcohols or with two or more compounds (3) or two or more trihalogenated silanes (4), having two or more different aliphatic hydrocarbon groups represented as $R^1$.

The functional substance-releasing agent containing the silicate ester compounds (1) and (2) of the present invention can gradually release the functional substance for a long time. When $R^2$ in the silicate ester compounds (1) and (2) is a residual group excluding a hydroxy group from a fragrance alcohol or antibacterial alcohol, the functional substance-releasing agent of the present invention can sustain an effect such as an aroma and an antibacterial effect for a long time. Therefore, it is useful as an aroma-sustaining agent and/or antibacterial property-sustaining agent.

The functional substance-releasing agent containing the silicate ester compounds (1) and (2) of the present invention can be formulated into various products, including, for example, non-aqueous solution-based products such as oil-based deodorizing fragrances, powder detergents, solid soaps, bathing agents, sanitary products (e.g., diaper) and aerosol deodorizing agents. Since the functional substance-releasing agent of the present invention has good storage stability in an aqueous solution, it also can be formulated into perfumes, colognes, aqueous solution-based deodorizing fragrances, laundry products such as a liquid detergent and a softener, dishwashing detergents, cosmetics such as a liquid soap and a skin lotion, hair cosmetics such as a shampoo, a rinse, a conditioner, and a styling product, and liquid bathing agents. The functional substance-releasing agent of the present invention enables to sustain release of the functional alcohol for a long time.

The composition containing the functional substance-releasing agent of the present invention can be used as a detergent composition, a softener composition, a fragrance composition, a deodorizing composition, and the like.

A content of the functional substance-releasing agent in the composition of the present invention is not specifically limited, and can be varied according to an intended use. When the composition of the present invention is used as a detergent composition or a softener composition, a content of the functional substance-releasing agent in the composition is preferably 0.001 to 10% by mass, and more preferably 0.01 to 5% by mass. When the composition of the present invention is used as a fragrance composition, the content is preferably 0.001 to 90% by mass, and more preferably 0.01 to 10% by mass. When the composition of the present invention is used as a deodorizing composition, the content is preferably 0.0001 to 10% by mass, and more preferably 0.001 to 5% by mass.

EXAMPLES

The following Examples demonstrate the present invention. Examples are intended to illustrate the present invention and not to limit the present invention.

Preparation Example 1

Preparation of a functional substance-releasing agent containing octylsilicic acid tris (2-phenylethyl)ester[tris (2-phenylethyloxy)octylsilane]

In a 200 mL four-neck flask, under nitrogen flow, 55.30 g of octyltriethoxysilane (0.20 ml), 65.99 g of 2-phenylethanol (0.54 mol), and 0.958 mL of 2.8% sodium methoxide in methanol were stirred for two hours at 115° C. with distilling off ethanol. After two hours, an inner pressure of the flask was gradually reduced to 8 kPa, and the mixture was stirred for additional three hours at 115 to 121° C. with distilling off ethanol. After three hours, the mixture was cooled and the reduced pressure was released. Then, the mixture was filtered to give 94.84 g of yellow oil containing octylsilicic acid tris(2-phenylethyl)ester. The resultant oil was analyzed by gas chromatography (hereinafter, referred to as GC). The result is shown in Table 1. From the result, contents of octylsilicic acid tris(2-phenylethyl)ester of the compound (1) and octylsilicic acid bis(2-phenylethyl)ethyl ester of the compound (2) were 68.8% and 24.7%, respectively. These contents of the compounds (1) and (2) refer amounts in silicate ester compounds esterified with a functional alcohol (The same applies to the following).

TABLE 1

| Result of GC analysis of preparation example 1 *[1] | area % |
| --- | --- |
| 2-phenylethanol | 2.9 |
| $C_8H_{17}Si(OEt)_3$ | 0.1 |
| $C_8H_{17}Si(OEt)_2(OEtPh)$ | 2.8 |
| $C_8H_{17}Si(OEt)(OEtPh)_2$ | 23.2 |
| $C_8H_{17}Si(OEtPh)_3$ | 64.7 |
| Condensate1 *[2] | 1.2 |
| Condensate2 *[3] | 2.2 |

*[1] Et represents an ethyl group, EtPh represents a 2-phenylethyl group.
*[2] $C_8H_{17}$—Si(OEtPh)$_2$-O—Si(OEtPh)(OEt)-$C_8H_{17}$
*[3] $C_8H_{17}$—Si(OEtPh)$_2$-O—Si(OEtPh)$_2$-$C_8H_{17}$ Preparation Example 2

Preparation of a functional substance-releasing agent containing dodecylsilicic acid tris(2-phenylethyl)ester[tris(2-phenylethyloxy)dodecylsilane]

In a 200 mL four-neck flask, under nitrogen flow, 50.36 g of dodecyltriethoxysilane (0.15 mol), 51.61 g of 2-phenylethanol (0.42 mol) and 1.537 mL of 2.8% sodium methoxide in methanol were stirred for two hours at 116° C. with distilling off ethanol. After two hours, an inner pressure of the flask was gradually reduced to 8 kPa, and the mixture was stirred for additional three hours at 116 to 121° C. with distilling off ethanol. After three hours, the mixture was cooled and the reduced pressure was released. Then, the mixture was filtered to give 81.33 g of yellow oil containing dodecylsilicic acid tris(2-phenylethyl)ester. The resultant oil was analyzed by GC. The result is shown in Table 2. From the result, contents of dodecylsilicic acid tris(2-phenylethyl)ester of the compound (1) and dodecylsilicic acid bis(2-phenylethyl)ethyl ester of the compound (2) were 75.1% and 19.8%, respectively.

TABLE 2

| Result of GC analysis of preparation example 2 *[1] | area % |
| --- | --- |
| 2-phenylethanol | 2.5 |
| $C_{12}H_{25}Si(OEt)_3$ | <0.1 |
| $C_{12}H_{25}Si(OEt)_2(OEtPh)$ | 1.7 |
| $C_{12}H_{25}Si(OEt)(OEtPh)_2$ | 18.4 |
| $C_{12}H_{25}Si(OEtPh)_3$ | 69.9 |
| Condensate1 *[2] | 0.9 |
| Condensate2 *[3] | 2.2 |

*[1] Et represents an ethyl group, EtPh represents a 2-phenylethyl group.
*[2] $C_{12}H_{25}$—Si(OEtPh)$_2$-O—Si(OEtPh)(OEt)-$C_{12}H_{25}$
*[3] $C_{12}H_{25}$—Si(OEtPh)$_2$-O—Si(OEtPh)$_2$-$C_{12}H_{25}$ Preparation Example 3

Preparation of a functional substance-releasing agent containing hexadecylsilicic acid tris(2-phenylethyl)ester[tris(2-phenylethyloxy)hexadecylsilane]

In a 200 mL four-neck flask, under nitrogen flow, 50.56 g of hexadecyltriethoxysilane (0.13 mol), 44.43 g of 2-phenylethanol (0.36 mol), and 0.375 mL of 2.8% sodium methoxide in methanol were stirred for two hours at 113 to 120° C. with distilling off ethanol. After two hours, an inner pressure of the flask was gradually reduced to 8 kPa, and the mixture was stirred for additional three hours at 120° C. with distilling off ethanol. After three hours, the mixture was cooled and the reduced pressure was released. Then, the mixture was filtered to give 77.52 g of yellow oil containing hexadecylsilicic acid tris(2-phenylethyl)ester. The resultant oil was analyzed by GC. The result is shown in Table 3. From the result, contents of hexadecylsilicic acid tris(2-phenylethyl)ester of the compound (1) and hexadecylsilicic acid bis(2-phenylethyl)ethyl ester of the compound (2) were 69.9% and 19.9%, respectively.

TABLE 3

| Result of GC analysis of preparation example 3 *[1] | area % |
| --- | --- |
| 2-phenylethanol | 4.4 |
| $C_{16}H_{33}Si(OEt)_3$ | 0.2 |
| $C_{16}H_{33}Si(OEt)_2(OEtPh)$ | 1.5 |
| $C_{16}H_{33}Si(OEt)(OEtPh)_2$ | 16.4 |
| $C_{16}H_{33}Si(OEtPh)_3$ | 57.6 |
| Condensate1 *[2] | 2.1 |
| Condensate2 *[3] | 4.8 |

*[1] Et represents an ethyl group, EtPh represents a 2-phenylethyl group.
*[2] $C_{16}H_{33}$—Si(OEtPh)$_2$-O—Si(OEtPh)(OEt)-$C_{16}H_{33}$
*[3] $C_{16}H_{33}$—Si(OEtPh)$_2$-O—Si(OEtPh)$_2$-$C_{15}H_{33}$ Preparation Example 4

Preparation of a functional substance-releasing agent containing octylsilicic acid trigeranylester[tris(3,7-dimethyl-octa-2,6-dienyloxy)octylsilane]

In a 300 mL four-neck flask, under nitrogen flow, 83.01 g of octyltriethoxysilane (0.30 mol), 127.76 g of geraniol (0.83 mol), and 0.857 mL of 2.8% sodium methoxide in methanol were stirred for 2.5 hours at 110 to 115° C. with distilling off ethanol. After 2.5 hours, an inner pressure of the flask was gradually reduced to 8 kPa, and the mixture was stirred for additional three hours at 110 to 119° C. with distilling off ethanol. After three hours, the mixture was cooled and the reduced pressure was released. Then, the mixture was filtered to give 173.61 g of yellow oil containing octylsilicic acid trigeranyl ester. The resultant oil was analyzed by GC. The result is shown in Table 4. From the result, contents of octylsilicic acid trigeranyl ester of the compound (1) and octylsilicic acid digeranyl ester of the compound (2) were 72.2% and 23.0%, respectively.

TABLE 4

| Result of GC analysis of preparation example 4 *[1] | area % |
| --- | --- |
| geraniol | 3.7 |
| $C_8H_{17}Si(OEt)_3$ | <0.1 |
| $C_8H_{17}Si(OEt)_2(OGer)$ | 2.2 |

TABLE 4-continued

| Result of GC analysis of preparation example 4 *[1] | area % |
|---|---|
| $C_8H_{17}Si(OEt)(OGer)_2$ | 21.4 |
| $C_8H_{17}Si(OGer)_3$ | 68.5 |
| Condensate1 *[2] | 0.7 |
| Condensate2 *[3] | 1.5 |

*[1] Et represents an ethyl group, Ger represents a residual group excluding a hydroxy group from geraniol.
*[2] $C_8H_{17}$—Si(OGer)$_2$-O—Si(OGer)(OEt)-$C_8H_{17}$
*[3] $C_8H_{17}$—Si(OGer)$_2$-O—Si(OGer)$_2$-$C_8H_{17}$ Preparation Example 5

Preparation of a functional substance-releasing agent containing dodecylsilicic acid trigeranyl ester[tris(3,7-dimethyl-octa-2,6-dienyloxy)dodecylsilane]

In a 100 mL four-neck flask, under nitrogen flow, 19.64 g of dodecyltriethoxysilane (59 mmol), 25.14 g of geraniol (163 mmol) and 0.168 mL of 2.8% sodium methoxide in methanol were stirred for two hours at 117 to 119° C. with distilling off ethanol. After two hours, an inner pressure of the flask was gradually reduced to 8 kPa, and the mixture was stirred for additional three hours at 115 to 120° C. with distilling off ethanol. After three hours, the mixture was cooled and the reduced pressure was released. Then, the mixture was filtered to give 36.68 g of yellow oil containing dodecylsilicic acid trigeranyl ester. The resultant oil was analyzed by GC. The result is shown in Table 5. From the result, contents of dodecylsilicic acid trigeranyl ester of the compound (1) and dodecylsilicic acid digeranyl ethyl ester of the compound (2) were 69.9% and 17.4%, respectively.

TABLE 5

| Result of GC analysis of preparation example 5 *[1] | area % |
|---|---|
| geraniol | 6.2 |
| $C_{12}H_{25}Si(OEt)_3$ | <0.1 |
| $C_{12}H_{25}Si(OEt)_2(OGer)$ | 1.4 |
| $C_{12}H_{25}Si(OEt)(OGer)_2$ | 15.4 |
| $C_{12}H_{25}Si(OGer)_3$ | 61.9 |
| Condensate1 *[2] | 3.3 |
| Condensate2 *[3] | 6.5 |

*[1] Et represents an ethyl group, Ger represents a residual group excluding a hydroxy group from geraniol.
*[2] $C_{12}H_{25}$—Si(OGer)$_2$-O—Si(OGer)(OEt)-$C_{12}H_{25}$
*[3] $C_{12}H_{25}$—Si(OGer)$_2$-O—Si(OGer)$_2$-$C_{12}H_{25}$ Preparation Example 6

Preparation of a functional substance-releasing agent containing octadecylsilicic acid tris(2-phenylethyl)ester[tris(2-phenylethyloxy)octadecylsilane]

In a 500 mL four-neck flask, 25.05 g of octadecyltrichlorosilane (64.6 mmol) and 100 mL of absolute dichloromethane were introduced and cooled to 3° C. To this was added a solution, which was previously prepared by mixing 24.87 g of 2-phenylethanol (203.6 mmol), 16.12 g of pyridine (203.8 mmol) and 60 mL of absolute dichloromethane, dropwise over 50 minutes. Then, an ice bath was taken off and the mixture was stirred for 2.5 hours at a room temperature (20° C.). After 2.5 hours, 10 g of ethanol was added to the mixture and the obtained mixture was transferred to a 500 mL separatory funnel. An organic layer was washed six times with 150 mL of ion-exchanged water, dried over absolute sodium sulfate, and evaporated under reduced pressure. A product was further treated for one hour at 110° C. under a reduced pressure of 13.3 Pa to give 40.07 g of colorless oil. From the result of GC analysis, contents of octadecylsilicic acid tris (2-phenylethyl)ester of the compound (1) and octadecylsilicic acid bis(2-phenylethyl)ethyl ester of the compound (2) were 84.9% and 1.1%, respectively.

Preparation Example 7

Preparation of a functional substance-releasing agent containing octadecylsilicic acid tris(cis-3-hexenyl)ester[tris(cis-3-hexenyloxy)octadecylsilane]

In a 1 L four-neck flask, 49.48 g of octadecyltrichlorosilane (0.13 mol) and 200 mL of absolute dichloromethane were introduced and cooled to 3° C. To this was added a solution, which had been previously prepared by mixing 40.24 g of cis-3-hexenol (0.40 mol), 31.17 g of pyridine (0.40 mol) and 150 mL of absolute dichloromethane, dropwise over 70 minutes. During addition of the solution, 50 mL of absolute dichloromethane was further added. Then, an ice bath was taken off and the mixture was stirred for 6 hours at a room temperature (20° C.). After 6 hours, to the mixture was added 20 g of ethanol and transferred to a 1 L separatory funnel. An organic layer was washed seven times with 200 mL of ion-exchanged water, dried over absolute sodium sulfate, and evaporated under reduced pressure. A product was further treated for one hour at 100° C. under a reduced pressure of 13.3 Pa to give 71.73 g of colorless oil. From the result of GC analysis, contents of octadecylsilicic acid tris(cis-3-hexenyl) ester of the compound (1) and octadecylsilicic acid bis(cis-3-hexenyl)ethyl ester of the compound (2) were 87.0% and 1.2%, respectively.

Preparation Example 8

Preparation of a functional substance-releasing agent containing methylsilicic acid tris(2-phenylethyl)ester [tris(2-phenylethyl)methylsilane]

In a 1 L five-neck flask, 25.02 g of methyltrichlorosilane (0.17 mol) and 170 mL of absolute dichloromethane were cooled to 3° C. To this was added a solution, which previously prepared by mixing 64.27 g of 2-phenylethanol (0.53 mol), 41.60 g of pyridine (0.53 mol) and 100 mL of absolute dichloromethane, dropwise over 95 minutes. During addition of the solution, 130 mL of absolute dichloromethane was further added. Then, an ice bath was taken off and the mixture was stirred for 75 minutes at a room temperature (22° C.). After 75 minutes, to the mixture was added 30 g of ethanol and transferred to a 1 L separatory funnel. An organic layer was washed six times with 200 mL of ion-exchanged water, dried over absolute sodium sulfate, and evaporated under a reduced pressure. A product was further treated for 30 minutes at 100° C. under a reduced pressure of 13.3 Pa, removing the volatile out, to obtain 71.73 g of a colorless oil. From the result of GC analysis, contents of methylsilicic acid tris(2-phenylethyl)ester of the compound (1) and methylsilicic acid bis(2-phenylethyl)ethyl ester of the compound (2) were 88.3% and 3.9%, respectively.

Examples 1 to 4 and Comparative Example 1

An unperfumed liquid softener A shown in Table 6 was prepared by the standard method. The softener A was mixed with functional substance-releasing agents of the present invention prepared in Preparation Examples 1 to 3 and 6 and a comparative functional substance-releasing agent prepared in Preparation Example 8 in an amount of 0.5% by mass to the softener A to give softener compositions. Softener compositions were sealed in 50 mL screw vials and stored in a thermostat bath at 40° C. for two weeks. Softener compositions were measured for amounts of fragrance alcohol (2-phenylethanol) before and after storage by HPLC (detecting device: UV) to determine a residual rate of silicate ester compounds. The results are shown in Table 7.

TABLE 6

| Unperfumed liquid softener A | Compounded amount (% by mass) |
|---|---|
| Cationic softening base[1] | 15 |
| Polyoxyethylene (20) lauryl ether | 3 |
| Calcium chloride | 0.05 |
| Dehydration condensate of 1.7 mole of hardened beef tallow fatty acid and 1 mol of glycerol | 1 |
| Ethanol | 0.25 |
| Ethylenediaminetetraaceric acid tetrasodium salt | 0.01 |
| Concentrated hydrohloric acid | Adequate amount |
| Ion-exchange water | Balance |

[1]prepared by dehydration condensation of N-(3-aminopropyl)-N-(2-hydroxyethyl)-N-methylamine and hardened beef tallow fatty acid at 1:1.9 molar ratio according to a known method.

TABLE 7

|  | Example 1 | Example 2 | Example 3 | Example 4 | Comparative example 1 |
|---|---|---|---|---|---|
| Kind of functional substance-releasing agent | Preparation example 1 | Preparation example 2 | Preparation example 3 | Preparation example 6 | Preparation example 8 |
| Residual rate of silicate ester compounds (%) | 52 | 98 | 97 | >98 | <1 (stored for one day) |

Examples 5 to 8 and Comparative Examples 2 to 3

Softener compositions similarly prepared as of Examples 1 to 4 and Comparative Example 1 and a softener composition prepared by adding phenylethyl alcohol in an amount of 0.5% by mass to the softener A were stored for two weeks at 40° C., and evaluated for sustainability of aroma before and after storage according to the following method. The results are shown in Table 8.

<Method for Evaluating Sustainability of Aroma>

24 cotton towels were previously washed with a Hitachi automatic washing machine NW-6CY using a commercially available weak-alkali detergent (Attack, Kao Corporation) five times and dried in a room to remove excess agents (detergent concentration: 0.0667% by mass, tap water used: 47 L, water temperature: 20° C., washing: 10 minutes, rinsing in stored water: two times).

In a National electric bucket N-BK2-A, a softener composition before or after two week storage at 40° C. was dissolved in 5 L of tap water so as to be 10 g of softener composition per 1.0 kg of fabric (preparation of treatment bath). One minute after, two cotton towels pretreated as described above were soaked therein for five minutes. The soaked towels were transferred to a National electric washing machine NA-35, and dewatered for three minutes. The dewatered towels were allowed to stand overnight in a room at about 20° C. for drying. The dried towels were folded in octavo and allowed to stand for one week in a room at about 20° C.

After dewatered, dried, and allowed to stand for one week, towels were subjected to a sensory evaluation based on the following rating by 10 specialists of phenylethyl alcohol perfume intensity. An average value was calculated and rated such that the average value of 3 was ⊚ (double circle), not less than 2.0 and less than 3.0 was ○ (circle), not less than 1.0 and less than 2.0 was Δ (triangle), and not less than 0 and less than 1.0 was X (cross).

Evaluation Rate

3: strong aroma of phenylethyl alcohol

2: distinct aroma of phenylethyl alcohol

1: uncertain aroma not recognizable as of phenylethyl alcohol

0: no aroma of phenylethyl alcohol

TABLE 8

|  |  | Example 5 | | Example 6 | | Example 7 | | Example 8 | | Comparative example 2 | | Comparative example 3 | |
|---|---|---|---|---|---|---|---|---|---|---|---|---|---|
| Kind of functional substance-releasing agent storage for 2 weeks at 40° C. | | Preparation example 1 | | Preparation example 2 | | Preparation example 3 | | Preparation example 6 | | Preparation example 8 | | Phenylethyl alcohol | |
| | | before | after | before | after | before | after | before | after | before | after | before | after |
| Result of sensory evaluation | after dewatering | ○ | ○ | ○ | ○ | ○ | ○ | ○ | ○ | ○ | ⊚ | ⊚ | ⊚ |
| | After drying | ○ | ○ | ○ | ○ | ○ | ○ | ○ | ○ | ○ | Δ | Δ | Δ |
| | after allowed to stand for one week | ○ | ○ | ○ | ○ | ○ | ○ | ○ | ○ | ○ | X | X | X |

As clearly seen in Table 8, in Comparative Examples 2 and 3, sustainability of aroma was reduced due to decomposition during storage. The functional substance-releasing agents of the present invention had good storage stability, and thus provided sustained aroma for a long time.

Examples 9 to 11

Softener compositions were prepared by adding functional substance-releasing agents of the present invention prepared in Preparation Example 4, 5 and 7 in an amount of 0.5% by mass to the softener A and similarly evaluated as in Examples 5 to 8. Results also showed the effect of the present invention.

The invention claimed is:

1. A functional substance-releasing agent, comprising a silicate ester compound represented by the following formula (1) in an amount of 35 to 95% by mass and a silicate ester compound represented by the following formula (2) in an amount of 0.5 to 35% by mass:

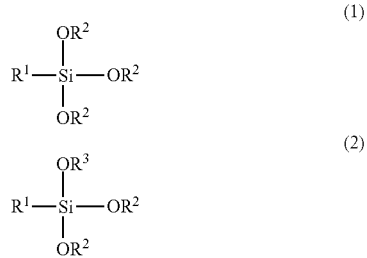

wherein $R^1$ represents an aliphatic hydrocarbon group having 10 to 18 carbon atoms in total that are optionally substituted with phenyl, hydroxy or an alkoxy group; $R^2$ represents a residual group excluding a hydroxy group from a functional alcohol, and a plurality of $R^2$s may be the same as or different from one another; and $R^3$ represents a hydrogen atom or an alkyl group having 1 to 6 carbon atoms.

2. The functional substance-releasing agent according to the claim 1, wherein the functional alcohol is a fragrance alcohol.

3. The functional substance-releasing agent according to the claim 1 or 2, being an aroma-sustaining agent.

4. A composition comprising, the functional substance-releasing agent according to claim 1.

5. A method for producing the functional substance-releasing agent according to claim 1, comprising conducting an interesterification between a compound represented by the following formula (3):

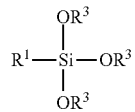

(wherein, $R^1$ and $R^3$ represent the same meaning as claim 1; and three $R^3$s may be the same as or different from one another)

and a functional alcohol.

6. A method for producing the functional substance-releasing agent according to claim 1, comprising conducting an esterification of a trihalogenated silane represented by the following formula (4):

(wherein, $R^1$ represents the same meaning as claim 1; and X represents a halogen atom) with a functional alcohol.

7. The functional substance-releasing agent according to the claim 1, wherein $R^1$ is a linear or branched alkyl group.

8. The functional substance-releasing agent according to the claim 1, wherein $R^1$ is a linear alkyl group.

9. The functional substance-releasing agent according to the claim 1, wherein $R^3$ is a methyl or ethyl group.

10. The functional substance-releasing agent according to the claim 1, wherein $R^3$ is an ethyl group.

11. The functional substance-releasing agent according to the claim 1, in which the amount of the silicate ester compound represented by the formula (1) is 45 to 95% by mass.

12. The functional substance-releasing agent according to the claim 1, in which the amount of the silicate ester compound represented by the formula (1) is 50 to 95% by mass.

13. The functional substance-releasing agent according to the claim 1, in which the amount of the silicate ester compound represented by the formula (2) is 10 to 30% by mass.

* * * * *